US006634335B2

(12) United States Patent
Boecking et al.

(10) Patent No.: US 6,634,335 B2
(45) Date of Patent: Oct. 21, 2003

(54) COMPONENT, ESPECIALLY A HIGH-PRESSURE COMPONENT FOR FUEL INJECTION SYSTEMS, AND METHOD FOR PRODUCING A COMPONENT OF THIS TYPE

(75) Inventors: Friedrich Boecking, Stuttgart (DE); Steffen Jung, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/980,507

(22) PCT Filed: Feb. 22, 2001

(86) PCT No.: PCT/DE01/00676

§ 371 (c)(1),
(2), (4) Date: Mar. 29, 2002

(87) PCT Pub. No.: WO01/69074

PCT Pub. Date: Sep. 20, 2001

(65) Prior Publication Data

US 2002/0113150 A1 Aug. 22, 2002

(30) Foreign Application Priority Data

Mar. 16, 2000 (DE) ........................................ 100 12 961

(51) Int. Cl.[7] ......................... F02M 37/04; A61L 41/08

(52) U.S. Cl. ..................... 123/456; 123/468; 285/133.4

(58) Field of Search ................................ 123/468, 469, 123/470, 456; 285/133.4, 197, 288.1, 382

(56) References Cited

U.S. PATENT DOCUMENTS

| | | | | | |
|---|---|---|---|---|---|
| 6,126,208 | A | * | 10/2000 | Asada et al. | 123/468 |
| 6,213,095 | B1 | * | 4/2001 | Asada et al. | 123/456 |
| 6,263,862 | B1 | * | 7/2001 | Asada et al. | 123/456 |
| 6,470,856 | B1 | * | 10/2002 | Boecking | 123/456 |
| 2002/0112697 | A1 | * | 8/2002 | Knoedl et al. | 123/456 |

FOREIGN PATENT DOCUMENTS

| | | |
|---|---|---|
| DE | 198 08 807 | 9/1998 |
| DE | 198 08 894 | 9/1998 |
| DE | 197 36 191 | 2/1999 |
| GB | 2 322 321 | 8/1998 |
| GB | 2 322 919 | 9/1998 |
| GB | 2 322 920 | 9/1998 |
| GB | 2 322 922 | 9/1998 |

* cited by examiner

*Primary Examiner*—Thomas N. Moulis
(74) *Attorney, Agent, or Firm*—Kenyon & Kenyon

(57) ABSTRACT

In a component, in particular a high-pressure part for a fuel injection system, having intersecting bores, at least one bore of the two intersecting bores is designed with a flat region, and the component has inherent compressive stresses in the area of the flat region of the bore. This yields an increase in strength of the component in the area of the intersection point of the two bores.

18 Claims, 2 Drawing Sheets

COMPONENT, ESPECIALLY A HIGH-PRESSURE COMPONENT FOR FUEL INJECTION SYSTEMS, AND METHOD FOR PRODUCING A COMPONENT OF THIS TYPE

FIELD OF THE INVENTION

The present invention relates to a component and a method for producing such a component.

BACKGROUND INFORMATION

The related art includes British Patent Nos. 2,322,919, 2,322,920, 2,322,321 and 2,322,922 as well as German Published Patent Application No. 198 08 894.

In conjunction with the present invention, a number of possible components which have intersecting bores in the interior, in particular CR injectors (CR=common rail) are of interest. Not only are these components under a very high internal pressure in the fuel injection system, but also the internal pressure is subject to great periodic fluctuations (pulsating internal pressure), so they must meet high strength requirements accordingly. The strength of the bore intersections is especially important.

SUMMARY OF THE INVENTION

An object of the present invention is to further increase the strength of bore intersections in components of the aforementioned type with respect to the internal compressive stresses that occur.

On the basis of the non-cutting shaping of the component in particular by pressure acting from the outside, a controlled flattening of the bore at the point of intersection of the respective bores can be achieved without any great technical complexity or cost expenditure.

The desired increase in the strength of the component is derived through inherent compressive stresses produced in a controlled manner directly at the most highly stressed point in the component, the bore intersections. Better utilization of the material is also achieved due to the increased strength of the component at these locations, which are exposed to extreme loads.

DETAILED DESCRIPTION

Figure 1:
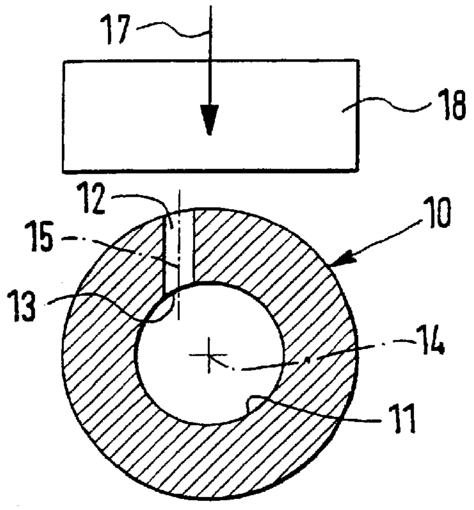
FIG. 1 shows an embodiment of a CR injector shown in cross section where the component is still undeformed.
Figure 2:
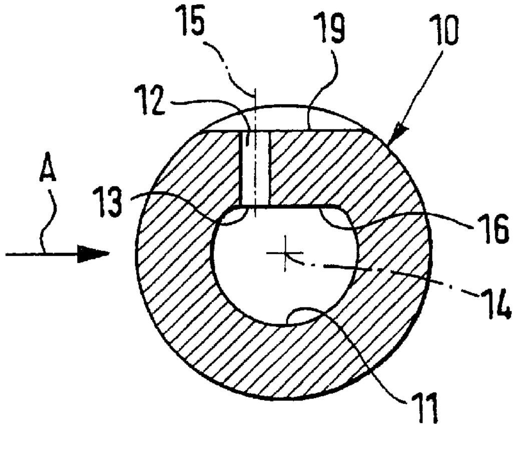
FIG. 2 shows the object from FIG. 1 shown in a cross-sectional diagram according to FIG. 1 (section II—II in FIG. 3) after non-cutting shaping of the component.
Figure 3:
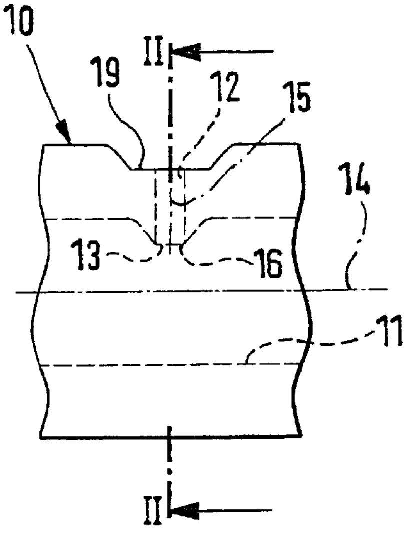
FIG. 3 shows the object from FIG. 2 as seen in the direction of arrow "A".

FIGS. 1 through 3 show an essentially cylindrical component 10 which is part of the CR injector. In its prefabricated state as shown in FIG. 1, component 10 has a continuous bore 11 with a circular cross section. A second bore 12 with a much smaller cross section opens at 13 into first bore 11 at a right angle to it. FIGS. 1 and 2 show clearly that central axes 14, 15 of two bores 11, 12 intersecting at 13 do not meet at the center of component 10. Second bore 12 thus opens eccentrically into first bore 11.

FIG. 2 shows that first bore 11 (still circular in the partially shaped state according to FIG. 1) has a flat region 16 in the area of intersection 13 of two bores 11, 12. Flat region 16 is the intentional result of non-cutting shaping of component 10 produced by pressure acting from the outside (in the direction of arrow 17) via a rectangular ram 18 (see FIG. 1).

As shown in FIGS. 2 and 3, this results in a groove-shaped deformation 19 on the outer circumference of component 10, although it is limited only to the area of second bore 12 and its intersection 13 with first bore 11, like flat region 16 produced by the pressure acting on it. Inherent compressive stresses thus build up in the area around intersection point 13, thereby greatly increasing the strength of component 10 in this area. The material area surrounding intersection point 13 of two bores 11, 12 meets extremely high strength requirements due to the pulsating compressive stress caused by the liquid medium (e.g., fuel) flowing through the bores.

Figure 4:
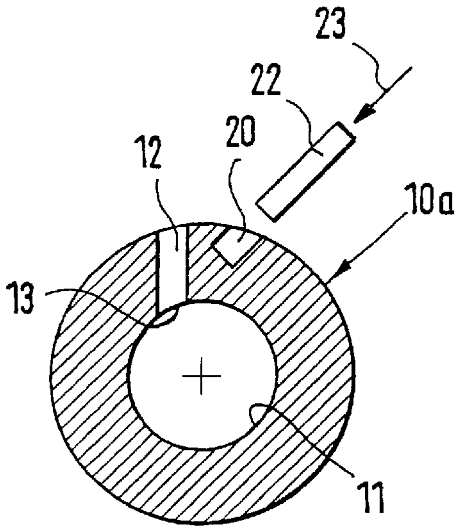
FIG. 4 shows a slightly modified variant of a CR injector in comparison with FIGS. 1 through 3, shown in a cross-sectional diagram according to FIG. 1 or 2, where the component is still undeformed.
Figure 5:
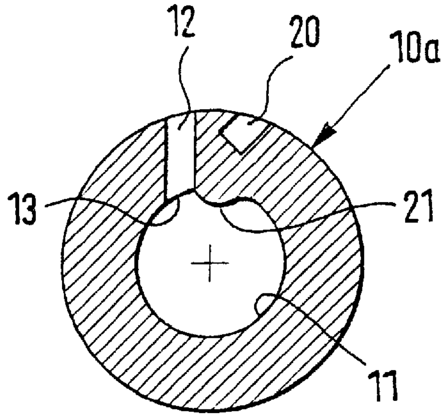
FIG. 5 shows the object from FIG. 4 shown in a corresponding cross-sectional diagram, but after non-cutting shaping of the component.

The component labeled 10*a* in FIGS. 4 and 5 is similar in design to component 10 in FIGS. 1 through 3. In particular, like the latter, it also has a continuous bore 11 with a large diameter and a second bore 12 with a much smaller diameter opening into the former eccentrically at a right angle. One difference in comparison with the embodiment according to FIGS. 1 through 3 is that in its processed state (FIG. 4), component 10*a* has a noncontinuous starting bore 20 which is directed at intersection point 13 of two bores 11, 12. To produce a local flat region 21 of bore 11 directly at opening point 13 of bore 12 (see FIG. 5), a ram 22 is inserted into starting bore 20 (see FIG. 4) and is acted upon by a force in the direction of arrow 23. Ram 22 may have a circular or oval cross section. With regard to the resulting increase in strength in the area of intersection point 13, the statements made in this regard concerning the embodiment according to FIGS. 1–3 are also applicable here accordingly.

Figure 6:
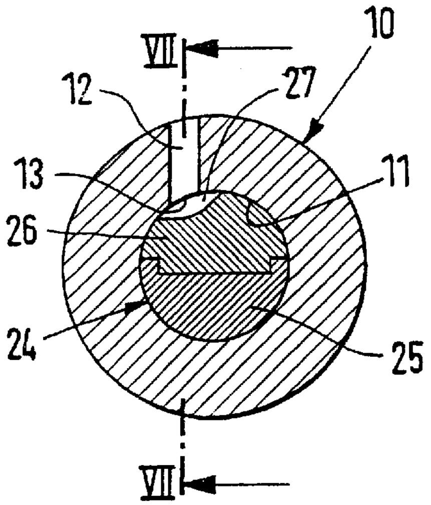
FIG. 6 shows a CR injector according to FIG. 1 in a corresponding cross-sectional diagram (section VI—VI in FIG. 7), with the female die inserted.
Figure 7:
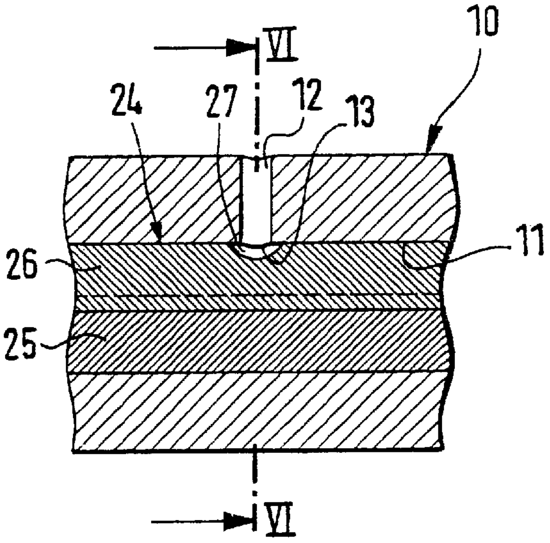
FIG. 7 shows a section along line VII—VII in FIG. 6.

One particular feature of the variant according to FIGS. 6 and 7 is that a female die labeled 24 on the whole is inserted into continuous bore 11 of component 10, which otherwise corresponds to the embodiment according to FIG. 1.

As shown in particular in FIG. 6, female die 24 is composed of two "halves" 25, 26 which are subdivided essentially horizontally and, when assembled, yield a circular cross section of female die 24 corresponding to the cross section of bore 11. Upper half 26 of female die 24 has a trough-shaped recess 27 at intersection point 13 of two bores 11, 12.

If, according to the embodiment illustrated in FIGS. 1 through 3, component 10 is acted upon by pressure in the direction of arrow 17 due to a ram 18 at the level of bore 12 (see FIG. 1), the material of component 10 is deformed according to the aforementioned shape of die recess 27 and into it so that a corresponding local flat region of bore 11 is formed (only) at intersection point 13 of two bores 11, 12. With regard to the resulting increase in strength in the area of intersection point 13, the statements made in this regard concerning the embodiments according to FIGS. 1 through 3 and FIGS. 4 through 5 are also applicable here accordingly. Female die 24 and trough-shaped recess 27 assist the shaping of the flat region and thus facilitate the development of the desired inherent compressive stresses in the material area of intersection point 13.

What is claimed is:

1. A component, comprising:

a structure including intersecting bores, wherein:

at least a first bore of the intersecting bores includes a flat region, at least a second bore of the intersecting bores intersects the first bore eccentrically; and the structure includes inherent compressive stresses in an area of the flat region of the at least first bore;

wherein an intersection of a central axis of the first bore and a central axis of the second bore is not located at a center of the component.

2. The component according to claim 1, wherein:

the component corresponds to a high-pressure part for a fuel injection system.

3. The component according to claim 1, wherein:

the at least first bore is continuous, a second bore of the intersecting bores opens into the at least first bore at an angle that is essentially 90°, and the flat region of the at least first bore is in a direction of opening of the second bore.

4. The component according to claim 1, wherein:

the flat region is arranged only in an area of an intersection point.

5. The component according to claim 1, wherein:

the intersecting bores have different diameters, and a diameter of the at least first bore is larger than diameters of remaining ones of the intersecting bores.

6. The component according to claim 5, wherein:

the diameter of the at least first bore is a multiple of a diameter of a second bore of the intersecting bores, only the at least first bore includes the flat region, and a cross section of the second bore is circular.

7. A component, comprising:

a structure including intersecting bores, wherein:

at least a first bore of the intersecting bores includes a flat region, and the structure includes inherent compressive stresses in an area of the flat region of the at least first bore;

wherein the intersection bores have different diameters, and a diameter of the at least first bore is larger than diameters of remaining ones of the intersecting bores;

wherein the diameter of the at least first bore is a multiple of a diameter of a second bore of the intersecting bores, only the at least first bore includes the flat region, and a cross section of the second bore is circular; and wherein the second bore opens eccentrically into the flat region of the at least first bore.

8. The component according to claim 6, wherein:

dimensions of the flat region are larger than the diameter of the second bore but are smaller than the diameter of the at least first bore.

9. A method of producing a component, comprising the steps of:

providing a structure including intersecting bores, each of the intersecting bores initially having a circular cross-section; and performing a non-cutting shaping of the structure in order to flatten at least a first one of the intersecting bores;

wherein a second bore of the intersecting bores intersects a first bore of the intersecting bores eccentrically; and wherein an intersection of a central axis of the first bore and a central axis of the second bore is not located at a center of the component.

10. The method according to claim 9, wherein:

the non-cutting shaping is performed when the structure is partially shaped.

11. The method according to claim 9, wherein:

the step of performing the non-cutting shaping produces a flat region, and the step of performing the non-cutting shaping is performed by a pressure acting on the structure from an outside.

12. The method according to claim 9, wherein:

the step of performing the non-cutting shaping is performed by a pressure acting on the structure via a ram approximately at a location of an outer lateral surface of the structure where the intersecting bores intersect in an interior.

13. The method according to claim 12, wherein:

the acting pressure is applied by a ram having dimensions that correspond approximately to desired contours of a flat region to be produced.

14. The method according to claim 12, wherein:

the acting pressure is applied by a ram having a rectangular cross section.

15. The method according to claim 12, wherein:

the acting pressure is applied by a ram having an essentially circular cross section, the ram being directed at an acute angle to one of the intersecting bores at a desired location of a flat region.

16. A method of producing a component, comprising the steps of:

providing a structure including intersecting bores, each of the intersecting bores initially having a circular cross-section;

performing a non-cutting shaping of the structure in order to flatten at least a first one of the intersecting bores; and prior to performing the non-cutting shaping, inserting a female die into one of the intersecting bores that is to be flattened, the female die including a recess corresponding to desired contours of a flat region at a location corresponding to a location of the flat region on the structure.

17. The method according to claim 12, wherein the acting pressure is applied by a ram having an essentially oval cross section, the ram directed at an acute angle to one of the intersecting bores at a desired location of a flat region.

18. The component according to claim 1, wherein the component has a groove deformation on an outer circumference of the component in an area of the second bore at an intersection with the first bore.

* * * * *